(12) United States Patent
Peyman (10) Patent No.: US 6,786,926 B2
(45) Date of Patent: Sep. 7, 2004

(54) METHOD AND APPARATUS FOR ALIGNMENT OF INTRACORNEAL INLAY

(75) Inventor: Gholam A. Peyman, New Orleans, LA (US)

(73) Assignee: Minu, L.L.C., Pittsboro, NC (US)

( * ) Notice: Subject to any disclaimer, the term of this patent is extended or adjusted under 35 U.S.C. 154(b) by 24 days.

(21) Appl. No.: 09/986,775

(22) Filed: Nov. 9, 2001

(65) Prior Publication Data

US 2003/0093083 A1 May 15, 2003

(51) Int. Cl.[7] .................................................. A61F 2/14
(52) U.S. Cl. ...................................... 623/5.11; 623/906
(58) Field of Search ............................ 623/5.11–5.16, 623/906, 4.1

(56) References Cited

U.S. PATENT DOCUMENTS

| | | | |
|---|---|---|---|
| 3,982,541 A | 9/1976 | L'Esperance, Jr. | |
| 4,298,004 A | 11/1981 | Schachar et al. | |
| 4,452,235 A | 6/1984 | Reynolds | |
| 4,607,617 A | * 8/1986 | Choyce ....................... 128/1 R | |
| 4,655,774 A | 4/1987 | Choyce | |
| 4,665,913 A | 5/1987 | L'Esperance, Jr. | |
| 4,669,466 A | 6/1987 | L'Esperance | |
| 4,676,790 A | 6/1987 | Kern | |
| 4,718,418 A | 1/1988 | L'Esperance, Jr. | |
| 4,729,372 A | 3/1988 | L'Esperance, Jr. | |
| 4,744,360 A | 5/1988 | Bath | |
| 4,807,623 A | 2/1989 | Lieberman | |
| 4,840,175 A | 6/1989 | Peyman | |
| 4,903,695 A | 2/1990 | Warner et al. | |
| 4,961,744 A | 10/1990 | Kilmer et al. | |
| 4,994,058 A | 2/1991 | Raven et al. | |
| 5,063,942 A | 11/1991 | Kilmer et al. | |
| 5,196,026 A | 3/1993 | Barrett et al. | |
| 5,215,104 A | 6/1993 | Steinert | |
| 5,269,812 A | * 12/1993 | White ............................ 623/5 | |
| 5,300,118 A | 4/1994 | Silvestrini et al. | |
| 5,318,044 A | 6/1994 | Kilmer et al. | |
| 5,318,047 A | 6/1994 | Davenport et al. | |
| 5,323,788 A | 6/1994 | Silvestrini et al. | |
| 5,336,261 A | 8/1994 | Barrett et al. | |
| 5,368,604 A | 11/1994 | Kilmer et al. | |
| 5,391,201 A | 2/1995 | Barrett et al. | |
| 5,403,335 A | 4/1995 | Loomas et al. | |
| 5,405,384 A | 4/1995 | Silvestrini | |
| 5,507,740 A | * 4/1996 | O'Donnell, Jr. ............... | 606/4 |
| 5,628,795 A | * 5/1997 | Langerman .................... | 623/6 |
| 5,697,923 A | * 12/1997 | Poler ............................. | 606/4 |
| 5,720,894 A | 2/1998 | Neev et al. | |
| 5,722,971 A | 3/1998 | Peyman | |
| 5,919,185 A | 7/1999 | Peyman | |
| 6,086,204 A | 7/2000 | Magnante | |
| 6,102,946 A | 8/2000 | Nigam | |
| 6,361,560 B1 | 3/2002 | Nigam | |
| 6,416,179 B1 | * 7/2002 | Lieberman et al. ......... | 351/212 |

OTHER PUBLICATIONS

Silverstrini, Pub. No. US2002/0010510 A1, Pub. Date Jan. 24, 2002, Variable Modulus Corneal Implant and Fabrication Method.*

Nigam, Pub. No. US2002/0029981 A1, Pub. Date Mar. 14, 2002, System for Packaging and Handling an Implant and Method of Use.*

(List continued on next page.)

Primary Examiner—Bruce Snow
Assistant Examiner—Cheryl Miller
(74) Attorney, Agent, or Firm—Roylance, Abrams, Berdo & Goodman L.L.P.

(57) ABSTRACT

A method of correcting refractive error in an eye, comprising the steps of marking at least one axis on the surface of the cornea. A portion of the cornea is then separated, forming a first anterior facing surface and a second posterior facing surface. An inlay having at least one axis indicated on the surface thereof is positioned between the first and second surfaces, and the at least one axis on the inlay is aligned with the at least one axis on the surface of the cornea. This results in precise positioning and orientation of the inlay and thus correction of astigmatic error in the cornea.

23 Claims, 6 Drawing Sheets

OTHER PUBLICATIONS

Karin R. Sletten, MD et al.; "An In Vivo Model of Femtosecond Laser Intrastromal Refractive Surgery", Experimental Science, Ophthalmic Surgery and Lasers, Nov./Dec. 1999, vol. 30, No. 9, pp. 742–749.

Griffith et al.; "Functional Human Corneal Equivalents Constructed from Cell Lines", SCIENCE, vol. 286, Dec. 10, 1999 pp. 2169–2172.

Yamauchi et al.; "Cultivation of fibroblast cells on keratin–coated substrata", Polymers for Tissue Engineering, pp. 329–340, VS 1998.

Ijima et al.; "Formation of a spherical multicellular aggregate (spheroid) of animal cells in the pores of polyurethane foam as a cell culture substratum and its application to a hybrid artificial liver", Polymers for Tissue Engineering, pp. 273–286, VSP 1998.

Cao et al.; "Comparative study of the use of poly(glycolic acid), calcium alginate and pluronics in the engineering of autologous porcine cartilage", Polymers for Tissue Engineering, pp. 315–327, VSP 1998.

Binder et al.; "Hydrogel keratophakia in non–human primates", Current Eye Research, vol. 1, No. 9, 1981/1982, pp. 535–542.

Swinger et al.; "Keratophakia and Keratomileusis—Clinical Results", American Academy of Opthalmology, Aug. 1981, vol. 88, No. 8, pp. 709–715.

L. Girard, "Corneal Surgery", The C.V. Mosby Publishing Company, London 1981 pp. 107–141.

Tadeusz Krwawicz, "Lamellar Corneal Stromectomy for the Operative Treatment of Myopia", Notes, Cases, Instruments, received in PTO–Sep. 1986, pp. 828–833.

Barraquer, "Keratomileusis and Keratophakia in the Surgical Correction of Aphakia", Cataract Surgery and Special Techniques prior to 1996, pp. 270–289.

Baumgartner et al., "Refractive Keratoplasty: Acute Morphologic Features," the CLAO Journal—Apr., 1985, vol. II, No. 2, pp 163–169.

Werblin, "Epikeratophakia: Techniques, Complications and Clinical Results", Ophthalmology, prior to 1996, pp. 45–58.

Sally Pobojewski, "New U–developed laser performs high–precision corneal surgery", News and Information Services, The University Record, Jul. 16, 1997.

\* cited by examiner

METHOD AND APPARATUS FOR ALIGNMENT OF INTRACORNEAL INLAY

FIELD OF THE INVENTION

The present invention relates to a method and apparatus for correcting the astigmatic refractive error in the cornea of the eye. In particular, the cornea is modified by forming a flap in the cornea and exposing a portion of the cornea underlying the flap. The exposed portion is marked and an asymmetric inlay having a thin removable, transparent sheet with markings indicated thereon is positioned on the exposed portion of the cornea. The markings on the cornea and those on the sheet are aligned to ensure proper positioning of the asymmetric inlay.

BACKGROUND OF THE INVENTION

A normal emetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused behind the retina.

An eye suffering from astigmatism has a defect in the lens or shape of the cornea. Therefore, an astigmatic eye is incapable of sharply focusing images on the retina.

Optical methods are known which involve the placement of lenses in front of the eye, for example, in the form of eyeglasses or contact lenses, to correct vision disorders. A common method of correcting myopia is to place a "minus" or concave lens in front of the eye to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses.

Although these optical methods can be used to correct vision in eyes suffering from low myopia, or in eyes suffering from hypermetropic, hyperopic or astigmatic conditions which are not very severe, these methods are ineffective in correcting vision in eyes suffering from severe forms of ametropia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then thawed and reattached to the main portion of the live cornea. Hence, it is intended that the reshaped cornea will change the position at which the light entering the eye through the cut portion is focused, so that hopefully the light is focused directly on the retina, thus remedying the ametropic condition.

The myopic keratomileusis technique is known to be effective in curing myopic conditions within a high range. However, the technique is impractical because it employs very complicated and time consuming freezing, cutting and thawing processes.

Keratophakia is another known surgical technique for correcting severe ametropic conditions of the eye by altering the shape of the eye's cornea. In this technique an artificial, organic or synthetic lens is implanted inside the cornea to thereby alter the shape of the cornea and thus change its refractive power. Accordingly, as with the myopic keratomileusis technique, it is desirable that the shape of the cornea be altered to a degree that allows light entering the eye to be focused correctly on the retina.

However, the conventional lenses and methods for type of correction are often impractical for correcting astigmatic error in the eye. Since an irregular shaped cornea or eye generally causes astigmatic error, to correct astigmatism an implanted lens must be a specific asymmetrical shape that would negate the irregularity. Often is difficult to properly position and maintain the lens in the correct orientation relative to the cornea, thereby making the procedure difficult and time consuming.

Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., and a publication by Jose I. Barraquer, M.D. entitled "Keratomileusis and Keratophakia in the Surgical Correction of Aphakia". The entire contents of each of these patents are incorporated herein by reference.

Surgical techniques involving the use of ultraviolet and shorter wavelength lasers to modify the shape of the cornea also are known. For example, excimer lasers, such as those described in U.S. Pat. No. 4,840,175 to Peyman, which emit pulsed ultraviolet radiation, can be used to decompose or photoablate tissue in the live cornea so as to reshape the cornea.

Specifically, a laser surgical technique known as laser in situ keratomileusis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is then reattached over the ablated portion of the cornea and assumes a shape conforming to that of the ablated portion.

However, because only a certain amount of cornea can be ablated without the remaining cornea becoming unstable or experiencing outwardbulging (eklasia), this technique is not especially effective in correcting very high myopia or large astigmatic error. That is, a typical live cornea is on average about 500 microns thick. The laser ablation technique requires that at least about 200 microns of the corneal stroma remain after the ablation is completed so that instability and outwardbulging does not occur. Hence, this method typically cannot be effectively used to correct high myopia or large astigmatic error, because, in order to reshape the cornea to the degree necessary to alter its refractive power to sufficiently correct the focusing of the eye, too much of the cornea would need to be ablated.

Other techniques exist for correcting astigmatic error using markings on a lens. However, these techniques generally only have a mark or multiple marks on a portion of the lens. This type of marking may indicate what direction the lens should be implanted in the cornea; however, they generally do not do not indicate where on the cornea they should be placed. For example, astigmatic correction is a relatively precise procedure and the lens must be placed both centrally on the cornea or at least in a predetermined position and oriented radially in the correct position, to negate the asymmetric shape of the cornea. The conventional procedures do not allow the proper alignment of the cornea surface and the lens implanted thereon. Therefore, existing procedures are inadequate to correct astigmatic error. Furthermore, many of these procedures have permanent markings on the lens, which may hinder the sight of the patient.

Therefore, it is apparent that a need therefore exists for improved methods for further modifying the cornea to better correct ametropic conditions, and more specifically to correct astigmatic error.

SUMMARY OF THE INVENTION

Accordingly, it is an object of the present invention to provide a method for adjusting the shape of a live cornea to correct high ametropic conditions.

Another object of the invention is to provide a method for modifying the shape of a live cornea to correct astigmatic conditions.

Yet another object of the present invention is to provide a method for adjusting the shape of a live cornea to correct astigmatic conditions by aligning the inlay with markings on the cornea.

Still another object of the present invention is to provide an intracorneal inlay having removable alignment markings thereon.

Still yet another object of the present invention is to provide an intracorneal inlay for correcting the refractive error in the eye having a removable, pliable sheet with markings thereon overlying at least a portion of the inlay to indicate the alignment of the inlay.

Further still it is another object of the present invention to provide an inlay for correcting the refractive error in the eye that is positioned under a flap in the cornea and aligned with markings on an exposed surface of the cornea.

The foregoing objects are basically attained by a method of correcting refractive error in the cornea of an eye, comprising the steps of marking at least one axis on the surface of the cornea, separating a portion of the cornea, forming a first anterior facing surface and a second posterior facing surface, positioning a inlay having at least one axis indicated on the surface thereof between the first and second surfaces, and aligning the at least one axis on the inlay with the at least one axis on the surface of the cornea.

The foregoing objects are further attained by an inlay for correcting the refractive error in the cornea of the eye, comprising a first surface for placement onto an exposed surface of the cornea, a second surface opposite the first surface, and a removable sheet of material overlying the second surface, the sheet having markings thereon for accurately positioning the inlay on the exposed surface of the cornea.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE INVENTION

As shown in FIGS. 1–17, the refractive properties of the eye can be modified or altered by placing markings 26 and 28 on both the external or outer surface 14 of the cornea 12 of an eye 10 and an internal surface 16, respectively. Surface 16 is generally exposed when a flap 18 is formed in the surface of the cornea. An inlay or implant 20 having a removable, pliable sheet 22 with markings 24 thereon is positioned on the exposed surface of the cornea, and the markings on the inlay are aligned with the markings 26 and 28. Preferably, this procedure is used for astigmatic correction, but may be used with any type of correction to the vision of the eye.

To begin, the refractive error in the eye is measured using wavefront technology, as is known to one of ordinary skill in the art. The refractive error measurements are used to determine the appropriate shape of lens or inlay 20 to best correct the error in the patient's cornea. Preferably, the inlay 20 is manufactured or shaped prior to the use of the wavefront technology and is stored in a sterilized manner until that specific inlay shape or size is needed. However, the information received during the measurements from the wavefront technology can be used to form the inlay using a cryolathe, or any other desired system or machine.

Figure 1:
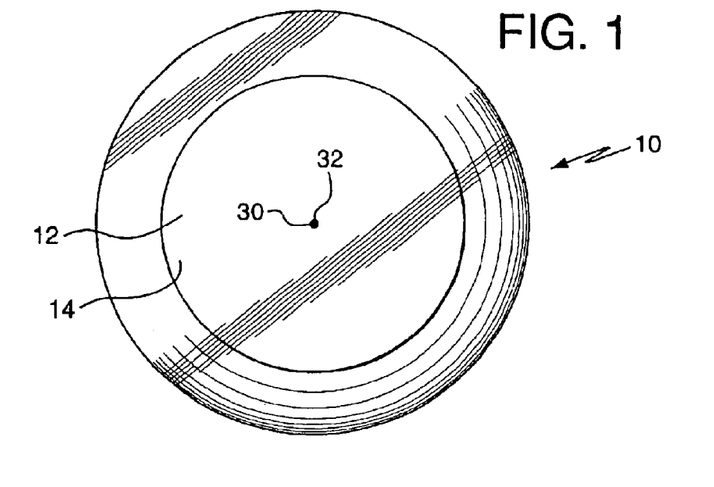
FIG. 1 is an elevational front view of an eye with the cornea marked along the main optical axis.

As seen in FIG. 1, the main optical axis or visual axis 30 of the eye is marked with a dot 32 or any other type of marking, such as cross-hairs or an X. The exact position of visual axis 30 of the eye 10 is determined by asking the patient to focus on a small beam of light, as is known in the art, and the location on the corneal surface is marked, using a marker (such as ink). Preferably, the ink is any conventional ink that is water-soluble and will be washed away after several blinks of the eye or application of water or any other suitable liquid, thus allowing unhindered sight by the patient.

Figure 2:
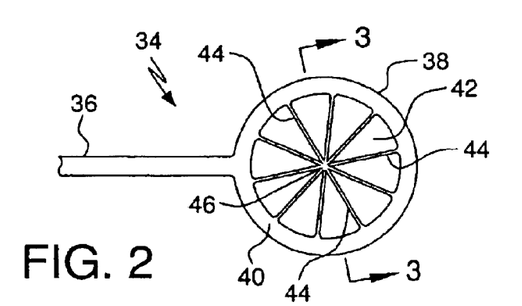
FIG. 2 is a plan top view of a marking device having 5 axes, according to the present invention.
Figure 3:
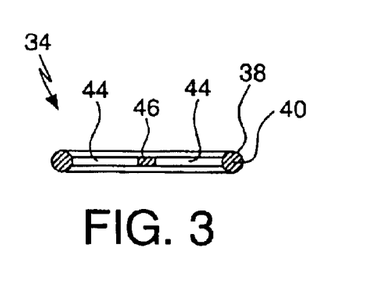
FIG. 3 is a side view in section of the marking device taken along lines 3—3 of FIG. 2.
Figure 4:
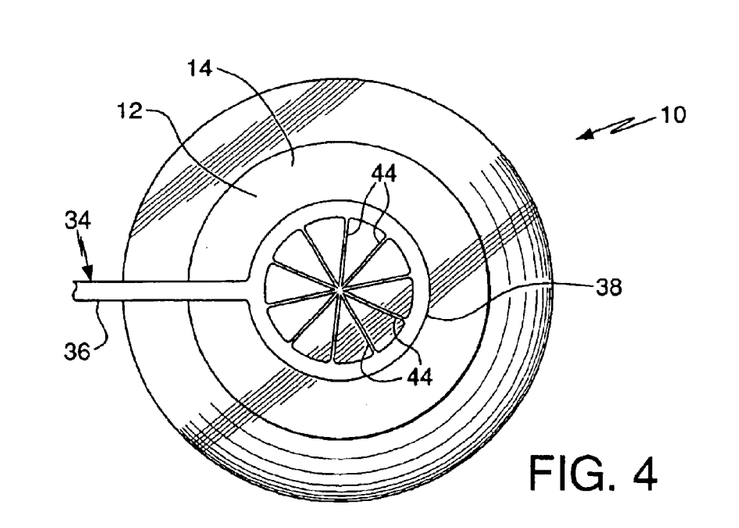
FIG. 4 is an elevational front view of the marking device of FIG. 2 overlying the eye of FIG. 1.

A marking device 34, as seen in FIGS. 2 and 3, can then be positioned adjacent the surface 12 of the cornea (FIG. 4). Device 34 is preferably formed of metal or plastic and has a handle 36 and a substantially circular head 38. Head 38 is formed of a substantially tubular or cylindrical portion 40 that extends from the handle 36 in a substantially circular manner, leaving an opening or area 42 within the tubular portion. Ten spokes 44 extend radially from a central portion 46 to the tubular portion 40 at equal intervals. In other words, the angle between each spoke 44 and the adjacent spoke is substantially equal to the angle between each other adjacent spoke. Spokes 44 define five separate axes or lines that extend from one portion of the tubular portion 40 to a side opposite or about 180 degrees therefrom. Each spoke is preferably substantially circular and in substantially the same plane as each other spoke. The spokes 44, however, do not necessarily need to be circular and spaced equally apart from one another and can number any number desired, for example they can number from one to as many can be fit into the desired area 42.

Figures 5, 6, 7:
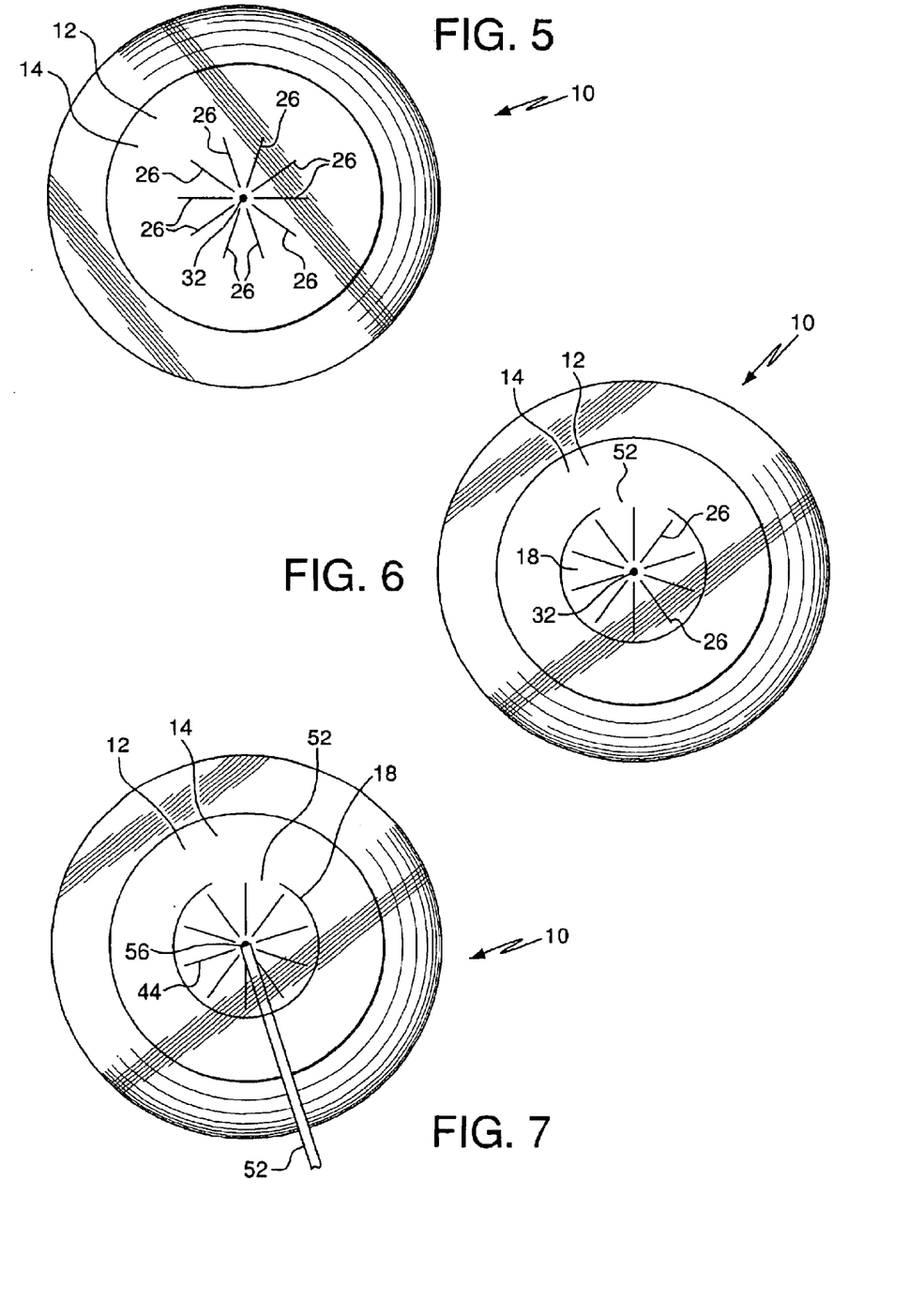
FIG. 5 is an elevational front view of the eye of FIG. 4 after markings were applied thereto by the marking device of FIG. 3.
FIG. 6 is an elevational front view of the eye of FIG. 5 with a flap formed in the surface of the cornea.
FIG. 7 is an elevational front view of the eye of FIG. 6 with a device marking the main optical axis under the flap.

Once the marking device 34 is positioned adjacent the external surface, the device 34 is centered using mark or dot 32. Water based or removable ink (substantially similar to the ink used to mark the visual axis) is then used to mark the surface 14 of the cornea 12 along the spokes 44. As seen in FIG. 5, this leaves ten lines 26 extending radially from dot 32 or five axes extending in separate directions. The lines 26 are in substantially the same configuration as the marking device spokes 44.

Preferably, flap or portion 18 can be formed in the surface 14 of the cornea 12, as seen in FIG. 6. The flap is formed in the stromal layer of the cornea, but does not necessarily need to be formed in the stromal layer and can be formed in any desired portion of the cornea. By forming the flap in the stromal laye, the cells of the cornea do not cause a gray to white response in the cornea, or protein detanurization The flap may be formed be any means desired, such as with a knife, microkeratome, or with a laser, such as a femtosecond laser or any other suitable laser.

Figure 8:
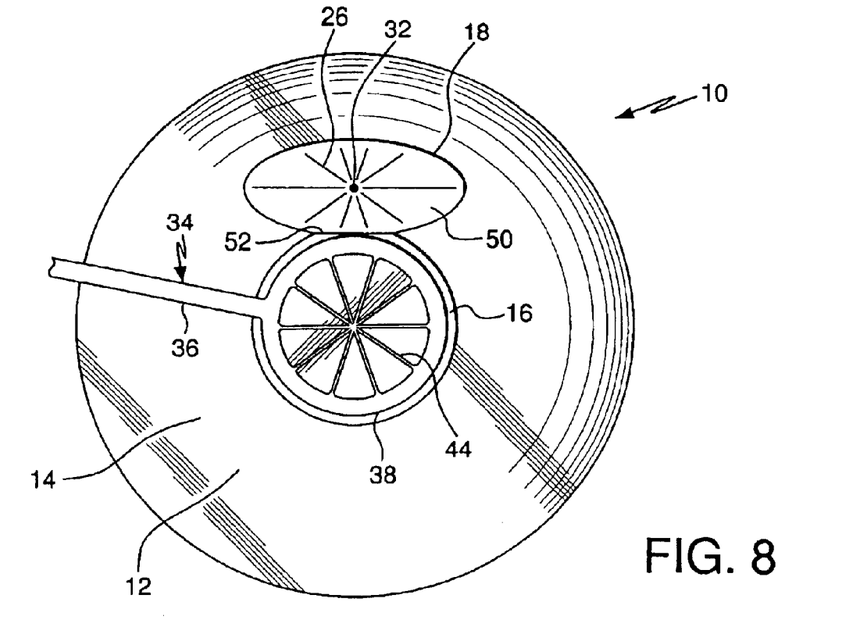
FIG. 8 is an elevational front view of the eye of FIG. 7 with the flap pivoted to expose a surface of the cornea and the marking device of FIG. 3 adjacent thereto.

Preferably, an internal area of the cornea is separated into first and second substantially circular shaped internal surfaces 16 and 50, respectively, as seen in FIG. 8, to form the circular shaped corneal flap 18. First internal surface 16 faces in an anterior direction of cornea 12 and the second internal surface 50 faces in posterior direction of the cornea 12. The flap 18 preferably has a uniform thickness of about 10–250 microns, and more preferably about 80–100 microns, but can be any suitable thickness. A portion 52 of flap 18 preferably remains attached to the cornea by an area at the periphery of the flap. However, the flap can be any suitable configuration, such as a flap attached to the cornea at a location other than at the periphery or a flap that is not attached to the cornea at all. Additionally, the flap may be shaped or sized as desired, and does not need to be circular.

As seen in FIG. 7, a tool or device or spatula needle 54 is inserted under the flap 18, in-between surfaces 16 and 50 and marks the main optical or visual axis 30. The mark 56 is preferably made on the first surface 16 and is lined up or positioned directly under or in about the same position as mark 32 on the external surface of the cornea.

The flap is moved or pivoted about portion 52 using any device known in the art, such as a spatula or microforceps or any other device, to expose the first and second corneal surfaces 16 and 50, respectively. The flap preferably exposes a portion of the corneal surface that intersects the main optical axis 30 and allows uninhibited access thereto.

Figure 9:
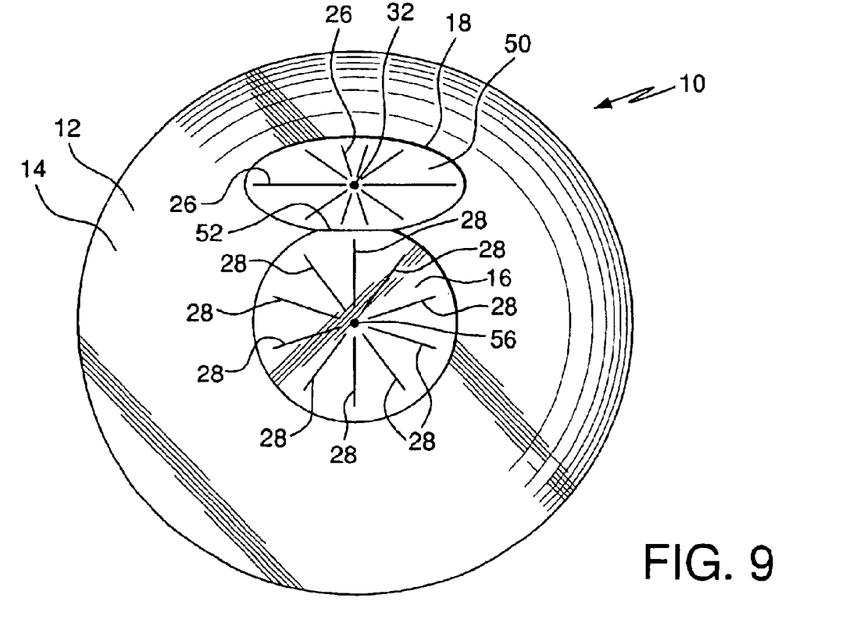
FIG. 9 is an elevational front view of the eye of FIG. 8 after markings are applied thereto by the marking device of FIG. 3.

Device 34 is positioned adjacent the exposed surface 16 and radial lines or axes 28 are made thereon using the removable ink, described above. Lines 28 are made in substantially the same positioning and placement as lines 26. In other words, lines 28 underlie lines 26, so that if flap 18 were replaced, lines 26 would overlie lines 28 and each overlying line would indicate substantially the same radian or axes. Lines 28 are formed in substantially the same manner as lines 26 and the description thereof applies to lines 28.

Figure 10:
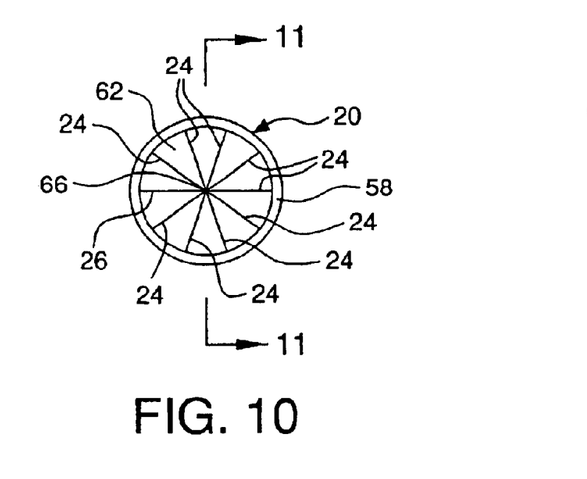
FIG. 10 is plan top view of an inlay according to the present invention with a pliable material overlying the inlay.
Figure 11:
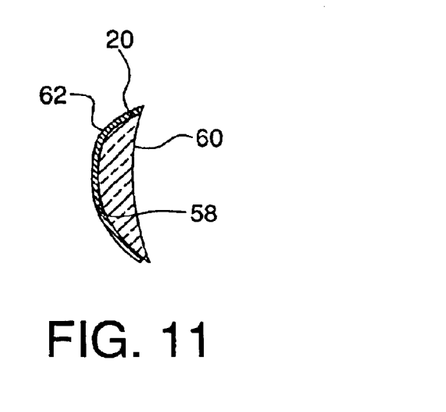
FIG. 11 is a side view in cross section taken along lines 11—11 of the inlay of FIG. 10.

As seen in FIGS. 10 and 11, inlay or lens 20 is preferably a substantially circular intracorneal inlay. Additionally, inlay 20 is preferably any polymer or hydrogel having about 70% to about 95% water content, and more preferably of about 78% to about 80% water content; however, the water content can be any percentage desired. The inlay may be formed from synthetic or organic material or a combination thereof. For example, the inlay can be collagen combined with or without cells; a mixture of synthetic material and corneal stromal cells; silicone or silicone mixed with collagen; methylmetacrylate; any transparent material, such as polyprolidine, polyvinylpylidine, polyethylenoxyde, etc.; or any deformable polymer, which can change its shape with radiation after implantation.

Furthermore, inlay 20 has a first side or surface 58 and a second side or surface 60, and is preferably shaped with an asymmetrical cross-section, as seen specifically in FIG. 11, so that it can correct astigmatic error in the eye. Preferably, as stated above, inlay 20 may come in many configurations and not necessarily that shown in FIG. 11, to correct many different degrees and variations of astigmatic error. Furthermore, inlay 20 may be used to correct hyperopia, myopia or any other vision problems or a combination of these vision problems and astigmatism.

Second surface 60 preferably is curved and pliable, so that it is able to conform to the first surface 16 of the cornea 12. The implant is preferably substantially circular, having a diameter of between about 2–10 mm and can have a refractive index different than that of the cornea or the same as that of the cornea. Preferably, the inlay has a refractive index of about 1.2 to 1.4, and more preferably of about 1.33. If the refractive index is the same as the cornea, the total refractive index of the cornea is altered after implantation of the inlay and repositioning of the flap. However, the inlay can be any size and/or configuration desired.

Furthermore, as seen in FIG. 11, a pliable or bendable sheet or film of transparent material 62 is positioned to overlie and conform to surface 58. Sheet 62 is preferably a synthetic material, such as any suitable polymer, and is substantially circular with markings or lines 24 thereon. Markings 24 have substantially the same positioning and placement as lines 26 and 28, or are 10 lines that radially extend from a center to form five separate axes. The description of lines 26 and 28 applies to markings 24. In other words, lines 24 are configured in such a manner that if the center of the markings 24 was placed on the marking 32 the lines can be adjusted or orientated so that markings 24 would overlie lines 28 and/or 26, each line indicating substantially the same radian or axis. Furthermore the center 66 of the markings 24 is preferably in the center of the inlay or positioned in any predetermined portion of the inlay.

Figure 14:
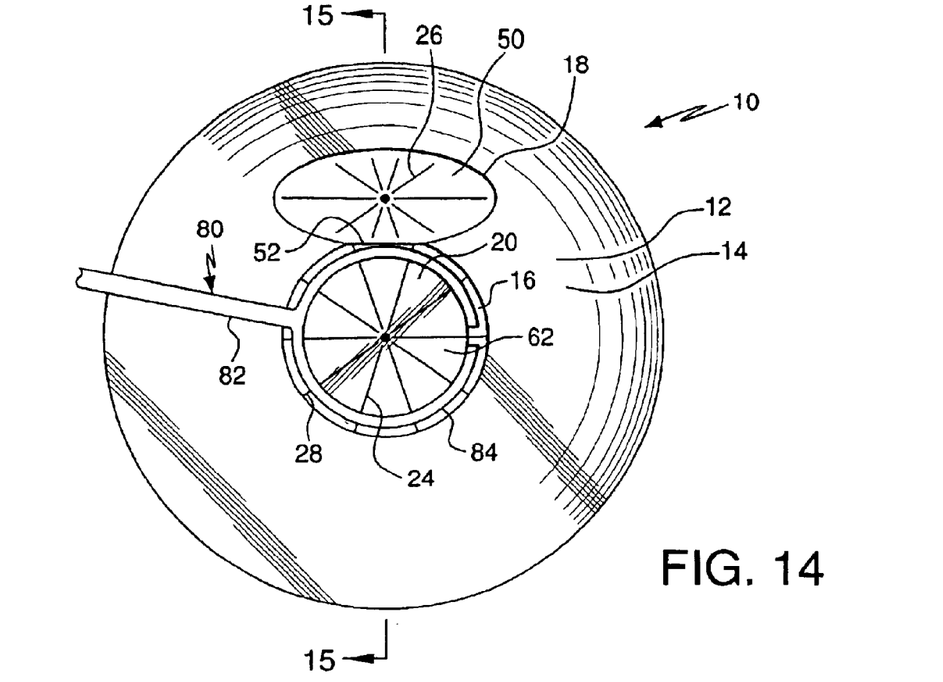
FIG. 14 is a elevational front view of the eye of FIG. 9 with the inlay of FIG. 10 positioned on an exposed surface of the cornea using the tool of FIG. 13.

This configuration of the lines and markings 28 and 24 allows the inlay to be placed on the exposed surface of the cornea directly over the visual axis 30 and oriented so that lines and markings 28 and 24 are precisely or substantially matched, as seen in FIG. 14. Furthermore, by placing the markings on the inlay and the cornea as described, an asymmetric astigmatic inlay can be correctly and accurately placed on the exposed surface of the cornea. It is generally crucial to the sight of the patient's eye, especially during astigmatic correction, to have the inlay precisely oriented to correct the existing error. If the inlay is not both centered over the visual axis, or at least positioned in a predetermined position over the visual axis, and oriented properly with respect to radial position, the inlay will not correct the desired astigmatic error and may even increase the refractive error in the cornea. Therefore, it can be seen that this inlay can be accurately positioned both radially and centrally on the eye to improve the vision of the eye.

Figure 12:
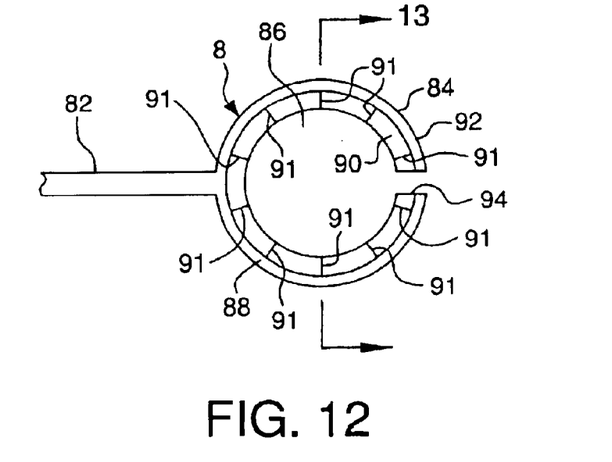
FIG. 12 is a plan top view of a tool for holding the inlay adjacent a corneal surface and positioning it thereon.
Figure 13:
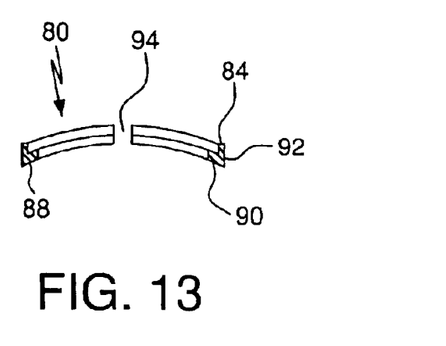
FIG. 13 is a side view on cross-section of the tool of FIG. 12 taken along lines 13—13.
Figure 15:
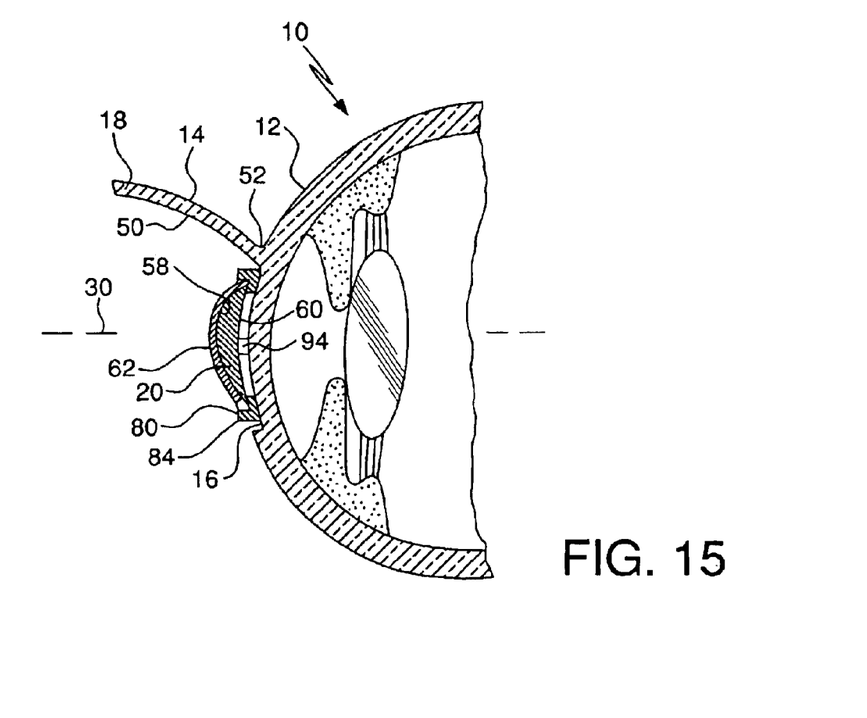
FIG. 15 is a side view in cross-section of the eye of FIG. 14 taken along lines 14—14.

Preferably, inlay 20 is positioned adjacent the surface of the cornea, using tool or holding device 80, in-between first and second corneal surfaces 16 and 50. As seen in FIGS. 12 and 13, tool 80 is preferably a plastic tool having a handle 82 and a substantially circular head 84; however, tool 80 can be any material and shape desired that would allow the placement of inlay 20 on a corneal surface. Head 84 has an open center portion 86 defined by an L-shaped holding portion 88, which is curved in a similar configuration as the surface of the cornea to facilitate positioning of the inlay; however, portion 88 can be straight or any other configuration desired. Portion 88 has a bottom wall 90 and a sidewall 92 that are sized and configured to hold inlay 20 therein (FIGS. 14 and 15). Additionally, wall 90 has markings or lines 91 that are substantially similar and oriented to the lines or markings 24 on the inlay. These markings allow the inlay to be aligned with the tool 80 when positioning the inlay adjacent the cornea. Furthermore, the walls 86 and 88 have an opening 94 at one end, preferably opposite or 180-degrees away from the handle 92. The opening allows the resilient head to separate and the inlay to be properly positioned in the exact or precise location desired on the exposed corneal surface, after it is aligned with the markings of the corneal surface, as described above.

It is noted that the inlay can be positioned without the use of tool 80, in any convention manner desired or any other manner, and does not necessarily need to be positioned on an internal surface of the cornea but may be placed or positioned on the external surface of the cornea.

Figure 16:
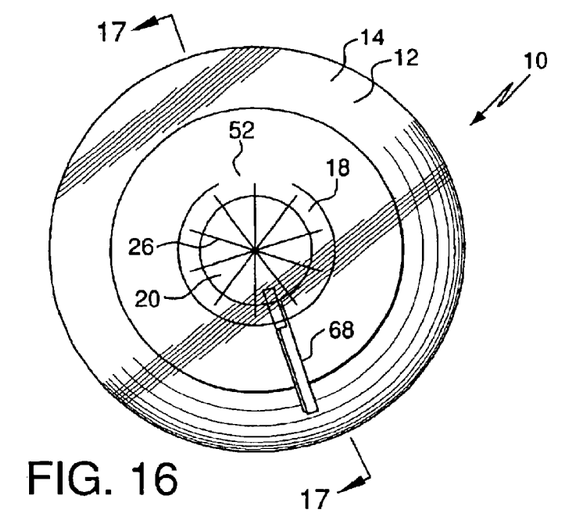
FIG. 16 is a elevational front view of the eye of FIG. 15 with the flap repositioned, the inlay aligned and a pair of forceps removing the pliable material from the surface of the inlay.
Figure 17:
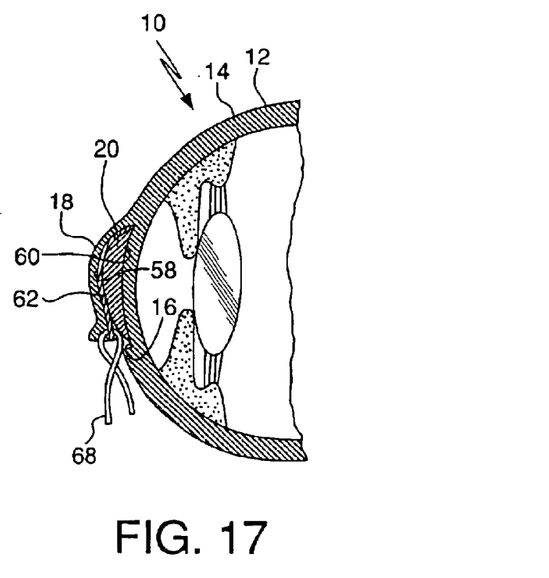
FIG. 17 is a side view in cross section of FIG. 16, taken along lines 17—17.
Figure 18:
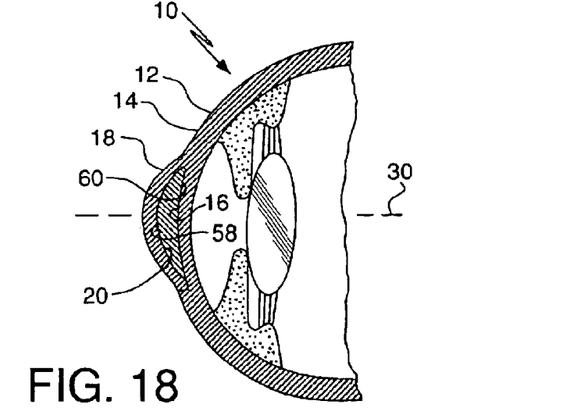
FIG. 18 is a side view in section of the eye if FIG. 17 after the pliable material has been removed.

Once tool 80 is removed and the inlay properly positioned, the flap 18 is replaced so that it covers or lies over the sheet 62 in a relaxed state, as seen in FIGS. 16 and 17. In other words, inlay 20 or sheet 62 does not force flap 18 away from the internal surface 58 and therefore the refractive properties of the cornea are not altered due to a tension force being applied to the flap. Preferably, the flap 18, the inlay 20, the visual axis 30 and surface 16 are all precisely lined up using the above described markings and lines. If any markings are off, the inlay and/or the flap can be repositioned by using small forceps. The forceps can be extended underneath the flap 18 to move the inlay with respect to the visual axis either in a rotational or a linear manner.

As seen in FIGS. 16 and 17, forceps 68 are used in grasp the sheet 62 and remove the sheet from the surface of the inlay, thus removing any markings on the inlay 20 that may hinder sight. Additionally, the markings on the eye would wash away after a short period of time due to the liquids developed naturally by the eye; however, if desired the ink my be washed of manually with the application of water or any other suitable liquid. Furthermore, it is noted that the sheet does not necessarily need to be removed and can remain on the inlay even after the procedure is completed. The ink on sheet 62 may be removable in the same manner as the ink to mark the cornea and would thus wash off after a short time period.

Additionally, the markings may be placed directly on the inlay and do not necessarily need to be on a sheet. This type of marking would allow the same proper placement without the need to remove the sheet. As stated above, the ink forming the markings could be removable.

It is noted that the markings do not necessarily need to be in the configuration described and can be any type of markings desired. For example, the markings can be radial dots that are positioned along the desired axes or radians or they can be concentric circles or a single circle or any other polygon desired or configuration of marks or dots desired that would allow the matching of the inlay, flap and surface of the cornea in the manner described above. Furthermore, the markings do not need to be removable and can be permanent, whether they are made with ink or actual alterations to the cornea and/or inlay, or the markings can be any combination of removable and/or permanent markings.

Figure 19:
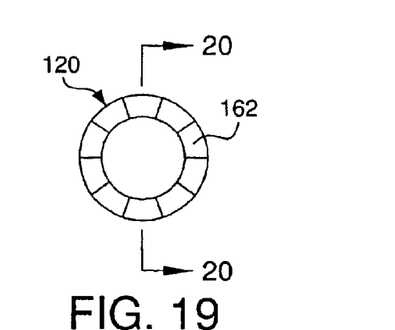
FIG. 19 is a plan top view of a ring shaped inlay suitable for the present procedure.
Figure 20:
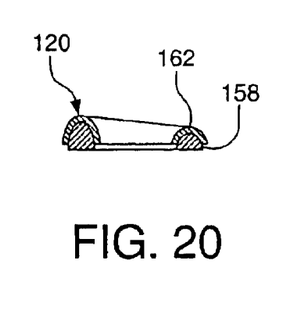
FIG. 20 is a side cross sectional view of the inlay of FIG. 19 taken along lines 20—20.

As seen in FIGS. 19 and 20, the inlay can be a ring-shaped inlay 120 with first and second surfaces 158 and 160. Inlay 120 is formed from substantially similar materials and therefore would have substantially similar properties to those of inlay 20 and therefore, the description thereof applies to the material and properties of inlay 120. As seen in FIG. 19, the inlay can have one portion that is larger than another portion, or in other words an asymmetric configuration that would correct astigmatic error as described above.

Inlay 120 can be used for correction of myopia or astigmatism or both. As with the above-described inlay, inlay 120 has a sheet of pliable, transparent material 162 overlying surface 158. However, sheet 162 is preferably ring-shaped and covers the ring shaped portion of inlay 120.

Furthermore, as with sheet 62, sheet 162 can be used to position and orientate inlay 120 relative to both the corneal flap 18 and the corneal surface 16 and the visual axis 30, as described above. Sheet 162 can also be removed in a similar manner as to that described above for sheet 62.

Figure 21:
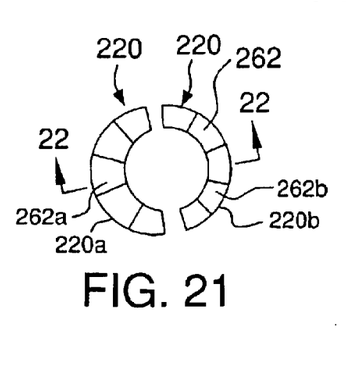
FIG. 21 is a plan top view of a two-piece ring shaped inlay suitable for the present procedure.
Figure 22:
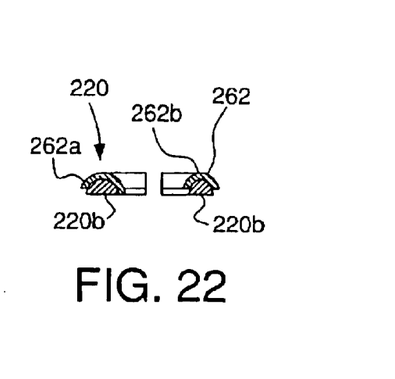
FIG. 22 is a side cross sectional view of the inlay of FIG. 21 taken along lines 22—22.

As seen in FIGS. 21 and 22, inlay 220 can be a ring-shaped inlay similar to inlay 120 but with portion portions 220*a* and 220*b*. As seen specifically in FIG. 22, portion of the inlay 220*a* can be larger than portion 220*b* for correction of astigmatic error, as described above. Furthermore sheet 262 can overlie the inlay in a similar manner as sheet 162. However, sheet 262 has two portions 262*a* and 262*b*, which overlie portions 220*a* and 220*b*, respectively. Inlay 220 is substantially similar to inlay 120 and inlay 20 and the descriptions thereof apply to inlay 220.

Additionally, the entire procedure for inlay 20 is applicable to both inlay 120 and inlay 220 and any description thereof is applicable to inlays 120 and 220.

While various advantageous embodiments have been chosen to illustrate the invention, it will be understood by those skilled in the art that various changes and modifications can be made therein without departing from the scope of the invention as defined in the appended claims.

What is claimed is:

1. An inlay for correcting the refractive error in the cornea of the eye, the cornea having a first exposed corneal surface and a second corneal surface, the inlay, comprising:

a first surface for placement onto the first exposed corneal surface, a second surface opposite the first surface, and a removable, pliable sheet of material positioned directly adjacent the second surface, said sheet overlying and conforming to the second surface and having markings thereon for accurately positioning the inlay on the first exposed corneal surface.

2. An inlay according to claim 1, wherein said markings on said removable sheet are at least ten radial axes extending from about the center of the inlay in a direction of the periphery of the inlay.

3. An inlay according to claim 1, wherein said inlay is asymmetric for the purpose of correcting astigmatic error in the eye.

4. An inlay according to claim 1, wherein said inlay is transparent, so that said markings can be aligned with markings of the first exposed corneal surface.

5. An inlay according to claim 1, wherein said inlay is pliable and is adapted to be positioned between the first and second corneal surfaces.

6. An inlay according to claim 5, wherein said markings on said removable sheet include radial markings and are adapted to align the inlay with markings on at least one of said first exposed and second corneal surfaces.

7. An inlay according to claim 1, wherein said markings on said removable sheet are radial markings and are adapted to align with a positioning tool to facilitate proper positioning of the inlay on the first exposed corneal surface.

8. An inlay according to claim 1, wherein said inlay has markings thereon, said markings including a mark on the center of the inlay and at least two radial axes extending from the center of the inlay in a direction toward the periphery of the inlay, and said markings are adapted to align with respective markings on at least one of said first exposed and second corneal surfaces.

9. An inlay for correcting refractive error in the cornea of the eye, the cornea having a first exposed corneal surface and a second corneal surface, the inlay, comprising:

a first surface and a second surface, at least one of said first and second surfaces having at least one removable marking thereon being extendable along at least one radial axis thereof, said at least one marking being adapted to align with a corresponding marking on at least one of the first and second corneal surfaces; and said at least one removable marking being disposed on a removable sheet of material directly overlying the second surface.

10. An inlay according to claim 9, wherein said at least one marking on said removable sheet includes at least ten radial axes extending from about the center of the inlay in a direction of the periphery of the inlay.

11. An inlay according to claim 9, wherein said at least one marking on said removable sheet includes at least one radial marking and said at least one marking is adapted to align with a positioning tool to facilitate proper positioning of the inlay on the first exposed corneal surface.

12. An inlay according to claim 9, wherein said inlay is asymmetric for the purpose of correcting astigmatic error in the eye.

13. An inlay according to claim 9, wherein said inlay is transparent, so that said at least one markings on said inlay can be aligned with said corresponding said at least one marking on the first exposed corneal surface.

14. An inlay according to claim 9, wherein said inlay and said removable sheet of material are pliable and adapted to be positioned between the first and second corneal surfaces.

15. An inlay according to claim 9, wherein said at least one marking includes a mark on the center of the inlay and at least two radial axes extending from the center of the inlay in a direction toward the periphery of the inlay, and said at least one markings are adapted to align with respective markings on the first and second corneal surfaces.

16. An inlay for correcting the refractive error in the cornea of the eye, the cornea having a first exposed corneal surface and a second corneal surface, the inlay, comprising:

a first surface for placement onto the first exposed corneal surface, a second surface opposite the first surface, and a removable, transparent, pliable sheet of material positioned directly adjacent overlying the second surface, said sheet overlying and conforming to the second surface and having markings thereon for accurately positioning the inlay on the first exposed corneal surface.

17. An inlay according to claim 16, wherein said markings on said removable sheet are at least ten radial axes extending from about the center of the inlay in a direction of the periphery of the inlay.

18. An inlay according to claim 16, wherein said inlay is asymmetric for the purpose of correcting astigmatic error in the eye.

19. An inlay according to claim 16, wherein said inlay is transparent, so that said markings can be aligned with markings on the first exposed corneal surface.

20. An inlay according to claim 16, wherein said inlay is pliable and is adapted to be positioned between the first and second corneal surfaces.

21. An inlay according to claim 20, wherein said markings on said removable sheet include radial markings and are adapted to align the inlay with markings on at least one of said first and second corneal surfaces.

22. An inlay according to claim 16, wherein said markings on said removable sheet are radial markings and are adapted to align with a positioning tool to facilitate proper positioning of the inlay on the first exposed corneal surface.

23. An inlay according to claim 16, wherein said inlay has markings thereon, said markings including include a mark on the center of the inlay and at least two radial axes extending from the center of the inlay in a direction toward the periphery of the inlay, and said markings are adapted to align with respective markings on the first exposed corneal surface.

\* \* \* \* \*